United States Patent [19]

Moussette

[11] 4,325,453

[45] Apr. 20, 1982

[54] PNEUMATIC HEADSET

[76] Inventor: Robert A. Moussette, 9C, Chinachem Commercial Centre, 272 Chatham Rd., Kowloon, Hong Kong

[21] Appl. No.: 158,516

[22] Filed: Jun. 11, 1980

[51] Int. Cl.³ .................................................. A61B 7/02
[52] U.S. Cl. ..................................................... 181/135
[58] Field of Search ................ 181/131, 135; 179/107; 73/585, 591, 649

[56] References Cited

U.S. PATENT DOCUMENTS 3,217,831  11/1965  Scanlon ............................... 181/135
3,303,902  2/1967   Knott .................................... 181/135

Primary Examiner—L. T. Hix
Assistant Examiner—Thomas H. Tarcza

Attorney, Agent, or Firm—Stevens, Davis, Miller & Mosher

[57] ABSTRACT

Disclosed is a pneumatic headset comprising a generally C-shaped frame having an upper portion designed to pass over a listener's head and downwardly extending leg portions. A pair of pneumatic sound tubes, each carrying a respective channel of audio information enters and is supported to a free end of one of the leg portions. A first shorter tube of the pair is connected to an earpiece located adjacent the point of tube pair entry into the frame, while a second longer tube is routed through the frame across the listener's head to another earpiece located opposed to the first. To balance sounds between the two earpieces, a venting port is provided in the shorter of the two tubes.

12 Claims, 5 Drawing Figures

PNEUMATIC HEADSET

BACKGROUND AND SUMMARY OF THE INVENTION

The present invention relates to the field of pneumatic headsets, particularly those which are used in the airline industry and supplied to passengers in flight to provided audio reception of one or more programs.

The type of pneumatic headset currently in use includes a generally U-shaped frame which fits under a passengers chin and supports respective ear pieces mounted on opposite ends of equal length acoustic sound tubes. The sound tubes are supported to and diverge from a common connection point located approximately centrally of the frame under a listener's chin to connect with the ear pieces. The pair of sound tubes are generally connected together upon exiting from the common portion of the pneumatic headset frame and terminate in an acoustic plug which is insertable in an acoustic sound source provided at a passenger seat location.

The problem with pneumatic headsets constructed as described above, is that they restrict passenger movement and are generally inconvenient because of the location of the acoustic sound tubes which emanate from the headset frame toward the plug. The location of the sound tubes under a listener's chin interferes with free head movement and also causes a general downward pull on the ear pieces and on a listener's ears.

An object of the present invention is to overcome these problems by providing a pneumatic headset which includes a generally C-shaped frame and associated head band connected thereto, the headband being adapted to fit on and over a passenger's head. A pair of acoustic sound tubes enter the frame at one side thereof and the tubes then separate, a shorter tube connecting with a first earpiece located on the side of the frame to which the sound tubes are commonly supported, and a longer tube extending over a passenger's head and supported by the frame to terminate at a second earpiece located at an opposite side of a listener's head. The sound tubes are commonly connected as they emerge from the frame and are also connected at their free ends to an acoustic plug as in conventional headsets.

With this arrangement, the headband supports the weight of the headset to eliminate the constant tugging downward on the frame and earpieces by the sound tubes as in conventional pneumatic headsets. In addition, by providing the sound tubes at one side of the headset, additional freedom in listener movement is afforded and a more comfortable and secure fit is attained.

In order to balance the sound radiating through the two earpieces of the headset from the longer and shorter sound tube, the present invention includes one or more sound venting ports provided in the shorter sound tube; that is, the sound tube connected to the earpiece closest the entry point of the pair of sound tubes into the frame. The porting of the shorter sound tube is accomplished by providing one or more small holes therein, either at a position adjacent the plug, or more preferably, at a position at the frame between the first earpiece and the entry point of the sound tubes into the frame.

A sound tube separator is provided at the entry point of the sound tubes into the frame to facilitate separation of the sound tubes and hold them in their separated states. The headset frame includes sidewalls and projections along the length thereof for guiding and holding the longer of the sound tubes in its path across a passenger's head. Each earpiece, in addition to being insertable onto the end of a respective tube, also includes annular projections thereon for engaging with respective annular grooves provided in the frame to insure positive holding of the ear pieces by the frame. The headband is attached on opposite sides of the frame in a manner which permits adjustment of the headband relative to the frame thus facilitating adjustment of the earpieces of the pneumatic headset relative to a listener's ears.

These and other features and advantages of the invention will be more fully appreciated by the following description of the invention which is taken in accordance with the accompanying drawings.

DETAILED DESCRIPTION OF THE INVENTION

Figure 1:
FIG. 1 is a perspective view of a pneumatic headset of the invention as worn by a listener.
Figure 3:
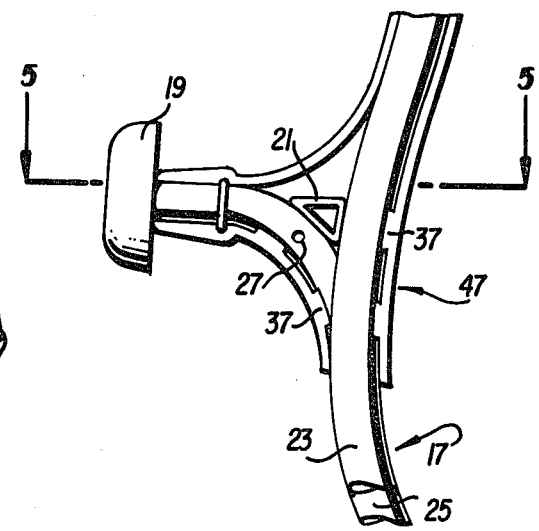
FIG. 3 is an enlarged view of a portion of FIG. 2.
Figure 4:
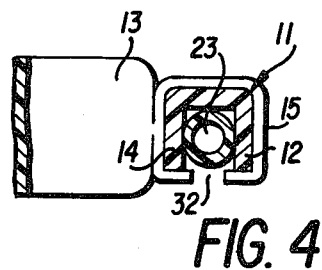
FIG. 4 is a sectional view along the lines 4—4 of FIG. 2.
Figure 5:
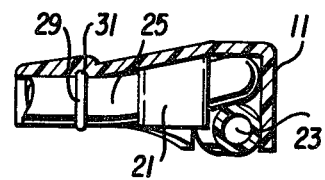
FIG. 5 is a sectional view along the lines 5—5 of FIG. 3.
Figure 2:
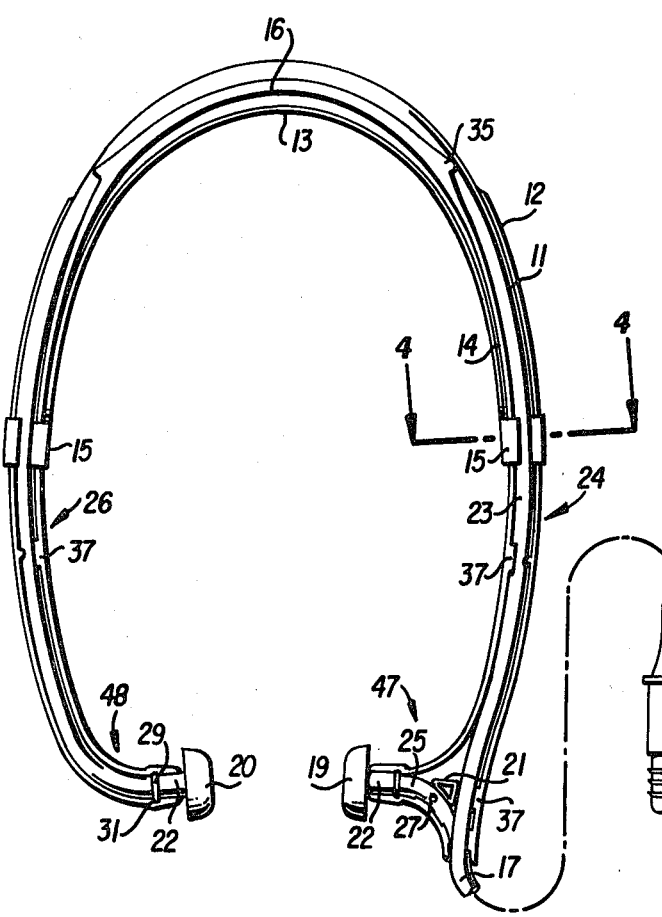
FIG. 2 is a rear view of the headset illustrated in FIG. 1.

The pneumatic headset of the invention as illustrated in the figures includes a conventional pneumatic sound tube pair 17, each designed to carry a respective channel of acoustic (audio) information to the ears of a listener. The sound tube pair 17 terminates at one end in a pneumatic sound tube plug 33 which is insertable in conventional manner into an acoustic transducing device supplying audio sounds. The pneumatic sound tube pair 17 is attached to a flexible frame 11 having a general C-shape which is designed to pass over the head of a listener. The frame 11 includes an upper portion 16 and downwardly extending leg portions 24 and 26 and can be made of any flexible material, such as plastics. The pneumatic sound tube pair 17 is supported by a side portion 47 of frame 11 at the free end of leg portion 24. Side portion 47 contains a triangular separator 21 for separating and guiding respective pneumatic sound tubes 25 and 23 of the pair along different paths. The shorter sound tube 25 is guided by the sidewalls of the frame 11 and the triangular separator 21 to an earpiece 19 which is attached to the end of sound tube 25. The longer sound tube 23 passes between sidewalls 12,14 of frame 11, over a listeners head, and is attached at its foremost end to an earpiece 20 provided at a free end portion 48 of frame leg 26 opposite portion 47.

The frame 11 sidewalls 12,14 and associated upstanding projecting portions 35 guide the second sound tube 23 as its traverses the length of the frame. The sidewalls along the downwardly extending legs 24,26 of frame 11 are dimensioned to provide a frictioned fit for the second sound tube 23 positively retaining it in place, while permitting its ready insertion into the frame during assembly. The projecting portions 35 provided on the upper portion 16 of frame 11 guides the second sound tube 23, but do not frictionally hold it, so that sound tube 23 is loosely retained as it passes over a listener's head. Consequently, when the earpieces are separated and frame 11 is flexed outwardly, expansion of the second sound tube at the top of frame 11 is possible, the second tube rising away from the upper portion 16 of frame 11. This ensures the second tube is not pushed downwards as the frame is outwardly flexed which might cause dislocation of the earpieces.

Each of the earpieces 19 and 20 has an interior bore which fits over the exterior periphery of the end of respective sound tubes 25 and 23. In addition, each earpiece includes, at the foremost end of a projection 22 which surrounds the respective sound tubes, an annular radially directed projection 29 which is engagable with an annular groove 31 provided in frame 11 at the terminating portion of the sound tubes 25 and 23. The projection 29 fits within an associated groove 31 to positively retain the earpieces 19 and 20 attached to frame 11 and to respective sound tubes 25 and 23.

In addition to the sidewalls of frame 11, pneumatic sound tubes 25 and 23 are also frictionally held in place by projecting elements 37 provided on the sidewalls of frame 11 and spaced therealong.

A flexible headband 13 is attached to frame 11 by clips 15 fixed to the headband which are slidable along the frame 11. The headband is slidable along frame 11 at clips 15 until a satisfactory adjustment of the earpieces 19 and 20 relative to a listener's ears is achieved. Enough friction is provided between the adjustable clips 15 and the frame to retain the headband in an adjusted position. This friction coupling can be provided by suitably dimensioning the interior of clips 15 relative to the exterior of frame 11 and can be enhanced by providing grooves or ridges on the sidewalls of frame 11 over which clips 15 pass. The headband can be formed of any flexible material, for example, plastics, while clips 15 can be made of a metal such as brass, or of a plastic. The clips 15 have an open side 32 to permit ready removal of the adjustable headband from the frame 11 for cleaning.

In order to balance the sound amplitudes exiting from respective earpieces 19 and 20, a sound venting hole 27 is provided in the shorter tube 25. This hole vents a portion of the acoustic energy traveling through sound tube 25 to the ambient atmosphere. By suitably dimensioning the diameter of hole 27, a balancing of the sounds emitted by earpieces 19 and 20 can be achieved. For example, if the inside diameter of each of the sound tubes is 4 mm and sound tube 23 is 15 inches longer than sound tube 25, a proper balancing of sound amplitudes from the earpieces occurs with a hole diameter of 1 mm. A preferred location for the hole is, as shown in FIG. 1, between the earpiece 19 and the portion of frame 11 where the sound tube pair 17 enters. Instead of providing holes 27 at the portion of tube 25 located between earpiece 19 and that portion of frame 11 where the sound tube pair 17 enters, it can be provided in sound tube 25 at the sound tube plug 33. It is preferable to provide the holes at one or the other extremes of the shorter sound tube 25 where it is not subject to flexing to insure adequate and consistent control of the venting of the sound and to avoid echo problems.

In lieu of a single hole, a plurality of holes 27 can be provided in sound tube 25, either between earpiece 19 and the entry point of sound tube pair 17 into the frame or at plug 33. Additional holes 27 could be furnished to improve, for example, the frequency response of the sounds emitted by earpiece 19.

As illustrated in FIG. 1, the frame 11 guides the sound tube pair 17 such that the plane of the sound tube pair, where it enters frame 11 is perpendicular to the general plane containing frame 11. This insures that the sound tube pair 17 is positioned relative to frame 11 in a manner which enables the sound tube pair to flex away from a listeners head thereby providing added listener head movement and improved comfort. In addition, by arranging the sound tube pair 17 to be substantially perpendicular to the plane of frame 11, the sound tube pair 11 can be easily wrapped about frame 11 without difficulty and without causing serious kinking.

While a preferred embodiment of the invention has been shown and described, it is to be understood that this embodiment is only exemplary of the invention and that numerous modifications can be made thereto without departing from the spirit and scope of the invention. Accordingly, the invention is not limited by the foregoing description, but is only limited by the claims appended hereto.

I claim:

1. A pneumatic headset comprising:
   a generally C-shaped frame having an upper portion adapted to pass over a listener's head and leg portions extending from said upper portion, the leg portions supporting respective sound channelling ear pieces at free ends thereof;
   a pair of sound tubes entering and commonly supported to one of the free ends of said frame, a first of said sound tubes being acoustically connected at one end thereof with one of said sound channelling earpieces closest to said one free end of said frame and a second of said sound tubes being supported along said frame and acoustically connected at one end thereof with the other of said sound channeling earpieces, such that sounds in said first and second sound tubes respectively pass through said earpieces, said first and second sound tubes extending equally from said one free end of said frame outward of said frame to an acoustic plug, for coupling said sound tubes to a source of acoustic sounds, said first sound tube containing at least one porting hole for balancing the amplitudes of sounds emitted by said earpieces.

2. A pneumatic headset as in claim 1 wherein said sound tubes are coupled together between said plug and frame and a tube separator is provided at said one free end of said frame for maintaining said tubes separated and for guiding said tubes toward respective paths in said frame.

3. A pneumatic headset as in claim 1 wherein said at least one porting hole is provided between said one earpiece and a point of entry of said sound tubes into said frame.

4. A pneumatic headset as in claim 3 wherein a plurality of holes are provided between said one earpiece and said point of entry.

5. A pneumatic headset as in claim 1 wherein said at least one hole is provided at said plug.

6. A pneumatic headset as in claim 5 wherein a plurality of holes are provided at said plug.

7. A pneumatic headset as in claim 1 wherein each said earpiece includes an annular outward projection and said frame includes, at opposite ends thereof, respective annular grooves for receiving said projections to mount said earpieces to said frame.

8. A pneumatic headset as in claim 1 further comprising a headband having opposite ends attached to said frame and extending over a portion of the length of said frame beneath said upper portion of said frame.

9. A pneumatic headset as in claim 8 wherein said headband is attached to said frame with adjustable clips.

10. A pneumatic headset as in claim 8 wherein said adjustable clips are fixed to said headband and are removable from said frame to permit separation of said headband from said frame.

11. A pneumatic headset as in claim 1 wherein said frame includes sidewalls in said leg portions for guiding and holding said second sound tube in said frame and said upper portion of said frame includes projections for loosely guiding said second sound tube over a listener's head.

12. A pneumatic headset as in claim 1 wherein said pair of sound tubes reside in a plane and said plane, as said sound tube pair exits said frame, is perpendicular to a plane in which said frame resides.

* * * * *